(12) United States Patent
Khanuja et al.

(10) Patent No.: US 6,824,795 B2
(45) Date of Patent: Nov. 30, 2004

(54) FORMULATION COMPRISING THYMOL USEFUL IN THE TREATMENT OF DRUG RESISTANT BACTERIAL INFECTIONS

(75) Inventors: Suman Preet Singh Khanuja, Lucknow (IN); Suchi Srivastava, Lucknow (IN); Ajit Kumar Shasney, Lucknow (IN); Mahendra Pandurang Darokar, Lucknow (IN); Tiruppadiripuliyur Ranganathan Santha Kumar, Lucknow (IN); Krishna Kumar Agarwal, Lucknow (IN); Ateeque Ahmed, Lucknow (IN); Nirmal Kumar Patra, Lucknow (IN); Prachi Sinha, Lucknow (IN); Sunita Dhawan, Lucknow (IN); Dharmendra Saikia, Lucknow (IN); Sushil Kumar, Lucknow (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/322,731

(22) Filed: Dec. 19, 2002

(65) Prior Publication Data

US 2003/0175283 A1 Sep. 18, 2003

Related U.S. Application Data

(62) Division of application No. 09/536,124, filed on Mar. 28, 2000, now Pat. No. 6,514,541.

(51) Int. Cl.[7] .............................................. A61K 35/78
(52) U.S. Cl. .................... 424/747; 424/725; 424/404
(58) Field of Search ................................ 424/747, 725, 424/404; 514/924

(56) References Cited

U.S. PATENT DOCUMENTS

| | | |
|---|---|---|
| 2,035,267 A | 3/1936 | Fleischman |
| 2,094,671 A | 10/1937 | Poetschke |
| PP1,614 P | 7/1957 | Murray |
| 3,518,343 A | 6/1970 | Welsh et al. |
| 3,821,117 A | 6/1974 | Breaece et al. |
| 3,936,385 A | 2/1976 | Cheng |
| 4,307,109 A | 12/1981 | Arbir et al. |
| 4,383,986 A | 5/1983 | Dubash et al. |
| 4,540,572 A | 9/1985 | Seth |
| 4,702,916 A | 10/1987 | Geria |
| 4,844,902 A | 7/1989 | Grohe |
| 4,847,071 A | 7/1989 | Bissett et al. |
| 4,863,725 A | 9/1989 | Deckner et al. |
| 4,925,655 A | 5/1990 | Smigel et al. |
| 5,073,366 A | 12/1991 | Beck |
| 5,411,733 A | 5/1995 | Hozumi et al. |
| 5,529,778 A | 6/1996 | Rohatgi |
| 5,801,153 A | 9/1998 | Badaway |
| 5,980,903 A | 11/1999 | Pruthi et al. |
| 6,127,405 A  * | 10/2000 | Kumar et al. ............... 514/450 |
| PP12,030 P2 | 8/2001 | Kumar et al. |

OTHER PUBLICATIONS

Mahfouz et al., Anz. Schadlingskde, Pflanzenschutz, Umweltschutz, (1995); 68: 82–84. Effect of essential oils of some medicinal plants on phytonematodes.

Sanyal et al., Indian J. Microbiology, (1969); 9(1): 23–24. In vitro antibacterial and antifungal activity of Mentha arvensis var. piperascens oil obtained from different sources.

Galitskii et al., Problemy Tuberkuleza, (1997); vol. O, No. 4: 35–38. Impact of phytotherapy on the prevention and elimination of hepatotoxic responses in patients with pulmonary tuberculosis, carriers of hepatitis B virusmarkers.

Srivastava et al., Acta Alimentaria, (Sep. 1999); 28(3): 291–295. GC–MS Investigation and antimicrobial activity of the essential oil of Carum Copticum Benth & Hook.

Syed et al., Pakistan J. Sci. Ind. Res., (Jun. 1986); 29(3): 189–192. Antimicrobial activity of the essential oils of Umbelliferae.

Chialva et al., J Essential Oil Research, (Jan.–Mar. 1993) 5: 105–106. Essential oil constituents of Trachyspermum copticum (L.) Link fruits.

Soliman et al., Egypt J. Pharm. Sci., (1997) 38(4–6): 553–564. A comparative study of the essential oils from certain Mentha and Salvia species grown in Egypt.

Lawrence et al., Perfum. Flavor. (1993); 18(3): 61–72. Progress in essential oils: Scoth peppermint oil.

Tucker et al., Econ. Bot. (1991); 45(2): 200–215. The origin of Mentha–gracilis Lamiceae II. Essential oils.

Molan, Bee Informed (1996); 3(2): 24–26. Honey for the treatment of infections.

* cited by examiner

Primary Examiner—Michele Flood
(74) Attorney, Agent, or Firm—Dinesh Agarwal, P.C.

(57) ABSTRACT

A formulation useful in the treatment of drug resistant bacterial infections comprising an effective amount of thymol obtained from the plant *Trachyspermum ammi*, mint oil containing an appropriate amount of monoterpenes obtained from a hybrid of *Mentha spicata* and *Mentha arvensis*, and conventional additives. A method for producing the formulation by mixing the above ingredients and a method for the treatment of drug resistance in a patient by administration of a therapeutically effective amount of the formulation.

6 Claims, No Drawings

FORMULATION COMPRISING THYMOL USEFUL IN THE TREATMENT OF DRUG RESISTANT BACTERIAL INFECTIONS

This is a division of application Ser. No. 09/536,124, filed Mar. 28, 2000, now U.S. Pat. No. 6,514,541, the contents of which are incorporated herein by reference.

FIELD OF THE INVENTION

The present invention relates to a novel synergistic composition useful in the treatment of drug resistant bacterial infections. The composition comprises an effective amount of thymol, a mixture of the essential oils of *Mentha arvensis* and *Mentha spicata* or their monoterpene components in appropriate ratio and conventional additives. The composition is useful in the treatment of drug resistant enteric and systemic infections. The formulation with enhanced activity of thymol action comprises thymol in combination with the oil which is a combination containing the rare mixture of carvone, limonene and menthol. The invention also provides methods of producing the composition and a method of using thymol obtained from the seeds of the plant *Trachyspermum ammi*(Ajwain) as a fourth generation antibiotic formulation for control of drug resistant bacteria. More particularly, the invention relate to the use of a compound 'Thymol' isolated from the oil distilled from the seeds of the plant *Trachyspermum ammi*(Ajwain) to kill the bacteria resistant to even prevalent third generation antibiotics and multi-drug resistant (mdr) microbial pathogens and thus useful as a plant based fourth generation herbal antibiotic formulation.

BACKGROUND OF THE INVENTION

Microbial infections are a major cause of human health hazards and misery leading to sizeable number of human deaths globally. In addition, the infections drastically affect human efficiency by incapacitating various metabolic functions and systems like digestive, respiratory, urinary, circulatory, nervous systems and skin. This then leads to continuous human suffering till the patient is completely cured of the causative microbes. Bacterial infections present a serious threat to the health and well being of people of all ages Antibiotics and antimicrobial drugs ever since the discovery of Penicillin by Alexander Fleming in the 1940s have been used by the medical practitioners to eliminate infective agents and curing the diseases. However, the infective microbes have always been able to fight back every new drug through development of resistance against the drug/antibiotic in use. Emergence of multiple drug resistant strains has appeared as a real problem in the field of medical science. The primary cause of the development of resistance is occurrence of random mutations. Mutations may occur in genes responsible for conferring sensitivity against a drug. With a relative dearth of new antibiotics with novel mode of action we may find ourselves on the verge of a medical disaster. It is high time to revive the hidden wonders of plant molecules with the modern tools of target based screening to develop newer advanced generation drugs and antibiotics with novel modes of actions.

Newer antimicrobials have been arising through structural modifications of existing agents leading to the development of higher generation drugs with wider spectrum of activity and enhanced potency. Well-exemplified cases for evolution of higher generation families of antimicrobial agents are penicillins and cephalosporins. These are evolved by the chemical modification of the basic β-lactam ring. Cephalosporin represents great-grand daughter-drug of cephalothin. Similarly, since the development of nalidixic acid as the first generation antimicrobial quinolone drug in 1962 by Lesher and colleagues, members of quinolone family have also evolved upto third generation. In fact, nalidixic acid found limited utility in treating systemic infections and subsequently marginally improved quinolones like oxolinic acid, pipemidic acid and cinoxacin were released in 1970's. Then came a breakthrough in early 1980's with the beginning of evolution of fluorinated quinolones. First to come up was norfloxacin, a second-generation quinolone having 6-fluorine and 7-piperazine substituents developed by Wolfson and Hooper. It had enhanced activity against both gram-negative and gram-positive bacteria like *Pseudomonas aeruginosa* and *Staphylococcus aureus*, respectively. This followed the development of sister drug molecules like ciprofloxacin, enoxacin, ofloxacin and pefloxacin etc. Almost concurrent has been the development of third generation agents such as lomefloxacin, fleroxacin, temafloxacin, tosufloxacin possessing one or more additional fluorine substituents as compared to second generation quinolones having a fluorine on position-6 on the basic quinolones.

Continuous and indiscriminate use of these quinolone/floroquinolone drugs is resulted into gradual insensitivity of the bacteria against whom these are used and thereby the pathogens requires more and more amount of these compounds as doses. Being synthetic, the use of these drugs results into forced side effects. Further, the pathogens are becoming resistant to even higher doses of these compounds to make the matter worse. To counter this problem, the applicants have developed a novel method of using the known plant based compound thymol in isolation to kill the drug resistant bacteria and also in combination with other available antibiotics to check the resistance development in the bacteria.

Considering the deadliest bacterial infections, tuberculosis is world's leading killer claiming more than three million lives world-wide every year. More appalling is the increased incidence of this disease and mortality among HIV positive individuals. The resurgence of tuberculosis and its incidence in human immuno-deficiency virus-positive populations in both developing and industrialized countries has focussed attention on the urgent need for development of new advanced generation drugs.

Current scenario of global awareness repeatedly flashes the ineffectiveness of the normally used antibiotics used for the cure of diseases like Tuberculosis. These problems are now assuming epidemic proportion even in the developing countries. New drug combinations using active molecules from natural sources like plants need to be systematically explored failing which the consequences are destined to be devastating and out of control for the human race in the new millennium. Among the most promising advances in the field of drug development is discovering new molecules or novel uses of the already available compounds with known safety and without any side effects. Such active biomolecules combined with other antibiotics can kill the drug resistant bacteria and simultaneously check further development of resistance in the infectious microbes.

Use of thymol in various herbal preparations ranging from mouthwashes and enteric disorders to skin infections is common. The parent oil and thymol itself as component of grandma's household recipes to treat a range of common ailments has found resident place because of being equally effective for children and adults. These uses have been exploited in the Indian subcontinent and also across the continents through formal and informal dissemination of traditional and herbal medicine knowledge.

Some of the related or prior art that need to be specifically cited here for establishing the uniqueness of our invention include the following different uses.

1. Composition for the treatment of viral infections including HIV (Pruthi et al. 1999; U.S. Pat. No. 5,980,903; Nov. 9, 1999) and its related arts (Badaway 1998; U.S. Pat. No. 5,801,153; September, 1998; Rohatgi 1996; U.S. Pat. No. 5,529,778; June, 1996; Hozumi et al. 1995; U.S. Pat. No. 5,411,733; May, 1995).
2. Analgesic composition useful in providing a temporary relief from symptoms of arthritis (Beck 1991; U.S. Pat. No. 5,073,366; Dec. 17, 1991) and its related arts (Arbir et al. 1981; U.S. Pat. No. 4,307,109; December, 1981; Dubash et al. 1983; U.S. Pat. No. 4,383,986; May, 1983; Seth 1985; U.S. Pat. No. 4,540,572; September, 1985; Geria 1987; U.S. Pat. No. 4,702,916; October, 1987; Grohe 1989; U.S. Pat. No. 4,844,902; July, 1989; Bisset et al. 1989; U.S. Pat. No. 4,847,071; July, 1989; Deckner et al. 1989; U.S. Pat. No. 4,863,725; July, 1989).
3. Powder composition for forming a mouthwash (Smigel et al. 1999; U.S. Pat. No. 4,925,655; Mat 15, 1990) and its related arts (Fleischman 1936; U.S. Pat. No. 2,035,267; March, 1936; Poetschke 1937; U.S. Pat. No. 2,094,671; October, 1937; Welsh et al. 1970; U.S. Pat. No. 3,518,343; June, 1970; Breece et al. 1974; U.S. Pat. No. 3,821,117; June, 1974; Cheng 1976; U.S. Pat. No. 3,936,385; February, 1976).

As evident from the cited references and literature search, none of the known inventions have mentioned or described the use of thymol and its compositions for treatment against drug resistant bacteria/microbes. But at the same time, its use/consumption by human system is well established and hence requiring no toxicological testing.

Accordingly, there is an urgent need for an effective, less expensive means of treating serious and life endangering bacterial infections, including TB, with minimal or nil side effects. The present invention addresses this compelling need nd provides a known herbal ingredient natural compound and its composition with other antibiotics/compounds for controlling bacterial agents, including Tuberculosis. Specific target based biological activity assays could define the novel use of a plant compound 'Thymol' isolated from the oil distilled from the seeds of the plant *Trachyspermum ammi* (Ajwain) to kill the bacteria resistant to even prevalent third generation antibiotics and multi-drug resistant (mdr) microbial pathogens. Thymol's nature and prey ous traditional use as well as the available information on human consumption indicate that it can be safely used as a plant based fourth generation herbal antibioti preparation. Accordingly, the applicants have worked on the enhancement of activity of thymol action and developed a novel formulation comprising thymol in combination with the appropriate combination of oils/monoterpenes from mints (*Mentha arvensis* and *M. spicata*) containing the rare combination of carvone, limonene and menthol.

The applicants have found entirely novel and far-reaching applications for overall aid to the human health care and fighting the microbial infections by drug resistant pathogens. The indiscriminate and excessive use of the common available antibiotics has been continuously leading to emergence of single and multiple drug resistance(s) in infectious agents. The applicants have taken the classes of drug resistance(s) in bacteria as the approach to classify them into categories of endangerment to human health, which is over and above the traditional taxonomic classes. The invention deals specifically with the drug resistant bacteria arising due to mutational events followed by selection due to continued presence of the said antibiotics. In the experiments, the applicants have used *Escherichia coli* and *Mycobacterium* as the model systems to monitor the evolution of resistance to quinolone and flouroquinolone drugs, mdr strain emergence and found out the novel use of the plant molecule (thymol) to kill the mdr strains and advanced generation drug resistant bacteria developed in continued presence of these drugs. This way this is a unique finding with great utility in the field of medicine.

OBJECTS

The main object of the invention is to provide a novel formulation useful in the treatment of drug resistant bacterial infections.

Another object of the invention is to provide a novel formulation comprising an effective amount of Thymol derived from the plant *Trachyspermum ammi* (Ajwain) and essential oil or monoterpene combination derived from *Mentha spicata* and *Mentha arvensis* useful in the treatment of bacterial infections.

Yet another is to provide methods for the preparation of the novel formulation of the invention.

Another object of the invention is to provide an antibacterial agent comprising Thymol, useful in the treatment of bacterial infections.

Still another object is to provide method of using Thymol for control of drug resistant bacteria.

SUMMARY OF THE INVENTION

The present invention provides a novel formulation comprising an effective amount of Thymol obtained from the plant *Trachyspermum ammi* (Ajwain), appropriate mint oil combination obtained from *Mentha spicata* and *Mentha arvensis*, and conventional additives. The invention also provides methods for the preparation of the novel formulation useful in the treatment of drug resistant bacterial infections. Further, the invention provides an anti-bacterial agent comprising an effective amount of Thymol, useful in controlling drug resistant bacteria. The invention also provides a method of using Thymol for control of drug resistant bacteria.

DETAILED DESCRIPTION OF THE INVENTION

The invention provides a novel synergistic formulation useful in the treatment of drug resistant bacterial infections, the formulation comprising an effective amount of 'Thymol' obtained from the plant *Trachyspermum ammi*, mint oil combination containing appropriate amounts of specific monoterpene obtained from *Mentha spicata* and *Mentha arvensis* and conventional additives.

In an embodiment Thymol is present in the range of about 100 to 500 mg or 20 to 50% w/w.

In yet another embodiment, mint oil combination is presented an amount of about 0.1 to 0.5 mg.

In still another embodiment, the additives are selected from the group comprising Citric acid present in the range of about 2–10 mg, Calcium carbonate present in the range of about 100–200 mg, Magnesium hydroxide gel present in the range of about 50–100 mg, Lactose present in the range of about 200–600 mg, honey in the range of about 0.1 to 1%, sodium glutamate present in the range of about 200 mg and sodium buffer.

In another embodiment, mint oil is diluted upto 10 times if desired.

In still another embodiment, the mint oil comprises Limonene in the range of about 6 to 25%, Menthol in the range of about 0.50 to 2.50% Carvone in the range of about 64.0 to 76%.

Yet another embodiment, comprises dilution of honey upto 10 times.

In still another embodiment, the formulation is effective against the group of bacteria selected from the genus *Mycobacterium* or *Escherchia*.

In yet another embodiment, the formulation is effective against bacteria resistant to drugs selected from the group comprising Ethidium bromide, Isoniazid, Chloremphenicol, Tetracycline, Rifampicin, Nalidixic acid, Oxolinic acid, Sparfloxicin, Ciprofloxicin and Loamfloxicin.

A novel synergistic formulation useful in the treatment of drug resistant bacterial infections, comprising an effective amount of 'Thymol' obtaine from the plant *Trachyspermum ammi*, mint oil obtained from a hybrid of *Mentha spicata* and *Mentha arvensis* and conventional additives.

It would be pertinent to note that the synergistic formulation of the invention exhibited surprising and unexpected anti-bacterial properties. The indiviual ingredients of the formulation do not have the property of the composition useful in the treatment of drug resistant bacterial infections. The present formulation comprising an effective amount-'Thymol' obtained from the plant *Trachyspermum ammi*, mint oil obtained from a hybrid of *Mentha spicata* and *Mentha arvensis* and conventional additives, exhibited surprising and unexpected anti-bacterial properties.

The formulation of the present invention may be derived in various physical forms such as tablets, syrup, powders, injections, etc. as are known in the art. In order to prepare such formulations in various physical forms, the essential ingredients of the formulation namely the compound Thymol and the essential oil combination having the desired monoterpene combination are mixed with conventional additives such as honey, sodium glutamate, citric acid and the like as mentioned above to increase clinical efficacy. It is also pertinent to note that the amounts of the respective ingredients of the formulation herein mentioned are only exemplary and appropriate amount of the respective ingredients will vary and may be readily determined by a person skilled in the art. The ratio of the amounts in the formulation of the present invention are not critical and vary widely. The best results would of course be obtained employing Thymol and specific mint oil combination in the proportion aforementioned. Optimal amounts of the ingredients of the formulation will vary with the method of administration of the formulation.

The invention also provides a method for the preparation of a formulation useful in the treatment of drug resistant bacterial infections, the method comprising the step of mixing an effective amount of Thymol oil obtained from the plant *Trachyspermum ammi*, combination of mint oils obtained from *Mentha spicata* and *Mentha arvensis* with conventional additives.

In an embodiment, Thymol is present in the range of about 100 to 500 mg or 20 to 50% w/w.

In another embodiment, mint oil is presented an amount of about 0.1 to 0.5 mg.

In still another embodiment, the additives are selected from the group comprising Citric acid present in the range of about 2–10 mg, Calcium carbonate present in the range of about 100–200 mg, Magnesium hydroxide gel present in the range of about 50–100 mg, Lactose present in the range of about 200–600 mg, honey in the range of about 0.1 to 1%, sodium glutamate present in the range of about 200 mg and sodium buffer.

In a further embodiment, mint oil is diluted upto 10 times if desired.

In yet another embodiment, the mint oil comprises Limonene in the range of about 6.8 to 23.2%, Menthol in the range of about 0.66 to 2.50% Carvone in the range of about 64.0 to 76.1%.

In still another embodiment, honey is optionally diluted upto 10 times.

In a further embodiment, the Thymol oil and the mint oil are dispersed in 0.1 to 1% honey to obtain a syrup.

In another embodiment, Thymol oil and the mint oil are mixed with Citric acid 2 to 10 mg and dissolved in a buffer containing sodium glutamate to obtain an injection.

In another embodiment, the formulation is effective against the group of bacteria selected from the genus *Mycobacterium* or *Escherchia*.

In yet another embodiment, the formulation is effective against bacteria resistant to drugs selected from the group comprising Ethidium bromide, Isoniazid, Chloremphenicol, Tetracycline, Rifampicin, Nalidixic acid, Oxolinic acid, Sparfloxicin, Ciprofloxicin and Loamfloxicin.

Further, the invention also provides a method for the treatment of drug resistant bacterial infections in humans comprising the steps of administration of a therapeutically effective amount of the novel formulation to a subject in need thereof.

In an embodiment, the formulation is administered through oral or subcutaneous routes.

In still another embodiment, the formulation is dissolved 5 ml 0.05 M Sodium buffer (pH 7.0) containing 200 mg sodium glutamate to be applied as subcutaneous injection.

In a further embodiment, the formulation is effective against bacterial infections such as enteric and systemic infections.

In yet another embodiment, the treatment comprises administration of the formulation for bacterial infections caused by bacteria resistant to drugs selected from the group comprising Ethidium bromide, Isoniazid, Chloremphenicol, Tetracycline, Rifampicin, Nalidixic acid, Oxolinic acid, Sparfloxicin, Ciprofloxicin and Loamfloxicin.

In an embodiment, the formulation is used for treatment of infections caused by multi-drug resistant bacteria selected from the genus *Mycobacterium* or *Escherchia*.

In still another embodiment, the formulation is used to kill bacteria resistant to the group of drugs comprising Ethidium bromide, Isoniazid, Chloremphenicol, Tetracycline, Rifampicin, Nalidixic acid, Oxolinic acid, Sparfloxicin, Ciprofloxicin and Loamfloxicin.

The present invention is the consequence of planned experimentation through specific activity bioevaluation assays. The intent of the investigation has been to ascertain and evaluate the potential of plant compound thymol from the oil of 'Ajwain' as the advanced generation antibiotic and development of a herbal antibiotic formulation with enhanced activity particularly the activity of killing drug resistant bacteria. The experiments progressed in finding this novel use following the first observation by us that the strains of *Escherichia coil* that had become resistant to nalidixic acid (a broad spectrum quinolone drug) due to mutations in the gyrA gene rather more sensitive to the *Trachyspermum ammi* oil and its major component 'thymol'.

The invention is described in detail by the following examples which should not be construed as limitations on the scope or sphere of the invention in any manner.

EXAMPLE 1

Antibacterial activity of the *Trachyspermum ammi* oil, thymol and non thymol fraction of the oil was determined in terms of growth inhibition zones produced on the bacterial lawn of drug resistant strains using disc diffusion assays (Table 1).

TABLE 1

Zone of inhibition (in mm) determined by disc diffusion assays

| E. coli strains | Trychyspermum ammi oil 50 mg/ml | Non-thymol oil fraction 50 mg/ml | Thymol 10 mg/ml | Thymol 20 mg/ml | Thymol 50 mg/ml |
|---|---|---|---|---|---|
| CA8000 | 4.5 | — | 1.0 | 2.0 | 5.0 |
| DH5α | 5.0 | — | 1.0 | 2.0 | 5.5 |
| ET8000 | 5.5 | — | 1.0 | 3.0 | 6.0 |

Here, CA 8000 is the wild type strain of *E. coli* while DH5α and ET 8000 harbor gyr mutations i.e. the gene encoding for the Gyr A subunit of DNA gyrase enzyme responsible for DNA relaxation is modified. These mutants are resistant to the quinolone because of the altered DNA gyrase. The specific mutations were confirmed through genetic complementation by transferring the plasmid cloned gyr A. As indicated in the table the killing zone of thymol is more in case of gyr mutant strains which are resistant to the above mentioned drugs. The activity was not observed in the non-thymol fraction of the oil.

EXAMPLE 2

Sensitivity of Nalidixic acid resistant strains of *Escherichia coli* to different antibiotics by poison agar method.

Independent mutants resistant to nalidixic acid were isolated in *E. coli* through induced and spontaneous mutagenesis in the wild type strain CA 8000. These were then tested for the sensitivity pattern not only against nalidixic acid but also the other quinolone and fluoroquinolone drugs of advanced generations since the resistance against the second and third generation drugs also arises due to the mutation(s) in the gyrA gene only. Table 2 below shows the pattern of cross-resistance pattern of such mutants

TABLE 2

Cross-resistance pattern of Nal$^R$ mutants of *E. coli*

Growth in poison agar medium containing

| Mutant (Nal$^R$) strains of *E. coli* | Nalidixic Acid 50 µg/ml | Oxolinic Acid 5 µg/ml | Sparfloxacin 5 µg/ml | Ciprofloxacin 5 µg/ml | Lomefloxacin 5 µg/ml |
|---|---|---|---|---|---|
| CAN 101 | + | − | + | − | − |
| CAN 102 | + | − | + | − | − |
| CAN 103 | + | − | + | − | − |
| CAN 104 | + | − | + | − | − |
| CAN 105 | + | − | + | − | − |
| CAN 106 | + | + | + | − | − |
| CAN 107 | + | + | + | − | − |
| CAN 108 | + | + | + | − | − |
| CAN 109 | + | + | + | − | − |
| CAN 110 | + | + | + | − | − |
| CAN 111 | + | + | + | − | − |
| CAN 112 | + | − | + | − | − |
| CAN 113 | + | + | + | − | − |
| CAN 114 | + | + | + | − | − |
| CAN 115 | + | + | + | − | − |
| CAN 116 | + | + | + | − | − |
| CAN 117 | + | + | + | − | − |
| CAN 118 | + | + | + | − | − |
| CAN 119 | + | − | + | − | − |
| CAN 120 | + | − | + | − | − |
| CAN 121 | + | + | + | − | − |
| CAN 122 | + | + | + | − | − |
| CAN 123 | + | + | + | − | − |
| CAN 124 | + | + | + | − | − |
| CAN 125 | + | + | + | − | − |
| CAN 126 | + | + | + | − | − |
| CA 8000 (WT) | − | − | − | − | − |

+ = Growth,
− = No growth,
WT = Wild Type

The nalidixic acid resistant strains isolated were grown in presence of different antibiotics as mentioned in the above table. These mutants showed positive growth in presence of high concentration of nalidixic acid. Some of them were also resistant to oxolinic acid and all to sparfloxacin but none of them were resistant to second generation drug ciprofloxacin and third generation drug lomefloxacin. The control wild type strain CA8000 as expected was sensitive to these antibiotics.

EXAMPLE 3

Bioevaluation of Thymol for Activity Against Nal$^R$ Mutants of *E. coli*

The above mutants were tested for the sensitivity against thymol to further confirm the above hypothesis that the Nal$^R$ mutants of *E. coli* can be killed by thymol rather more efficiently and hence indicating its use as a plant antibiotic to control drug resistant bacteria. Thymol in these assays clearly showed the activity against all the Nal$^R$ mutants whether it was single or multiple resistance (Table 3)

TABLE 3

Disk diffusion assay for determining the activity of thymol against nalidixic acid resistant mutants of *Escherichia coli*.

| Mutant (Nal$^R$) strains of *E. coli* | Thymol (inhibition zones in mm) | | |
|---|---|---|---|
| | 50 μg/disc | 100 μg/disc | 250 μg/disc |
| CAN 101 | Tr. | 1.5 | 4.0 |
| CAN 102 | Tr. | 2.0 | 7.0 |
| CAN 103 | Tr. | 2.0 | 4.0 |
| CAN 104 | Tr. | 2.0 | 6.0 |
| CAN 105 | Tr. | 2.0 | 5.0 |
| CAN 106 | 1 | 2.0 | 4.0 |
| CAN 107 | 1 | 3.0 | 5.0 |
| CAN 108 | Tr. | 2.0 | 5.0 |
| CAN 109 | 1 | 3.0 | 6.0 |
| CAN 110 | 1 | 3.0 | 6.0 |
| CAN 111 | 1 | 3.0 | 5.0 |
| CAN 112 | 1 | 3.0 | 5.0 |
| CAN 113 | Tr. | 2.0 | 5.0 |
| CAN 114 | 1 | 3.0 | 6.0 |
| CAN 115 | 1 | 3.0 | 5.0 |
| CAN 116 | 1 | 3.0 | 5.0 |
| CAN 117 | 1 | 3.0 | 5.0 |
| CAN 118 | 1 | 3.0 | 5.0 |
| CAN 119 | 1 | 3.0 | 6.0 |
| CAN 120 | 1 | 3.0 | 6.0 |
| CAN 121 | 1 | 3.0 | 5.0 |
| CAN 122 | Tr. | 2.0 | 5.0 |
| CAN 123 | 1 | 3.0 | 5.0 |
| CAN 124 | 1 | 3.0 | 5.0 |
| CAN 125 | 1 | 3.0 | 5.0 |
| CAN 126 | 1 | 2 | 5.0 |
| CA 8000 (WT) | 1 | 2 | 4 |

Tr = activity in traces (< 0.5 mm),
WT = Wild Type

In fact, the compound thymol was able to kill all the nalidixic acid resistant mutants of *E. coli* with greater efficiency than the wild type strain CA8000.

EXAMPLE 4

Isolation and Characterization of Mutants of *E. coli* Resistant to Lomefloxacin (third generation fluoroquinolone drug)

Induced mutants were isolated after selection in the presence of lomefloxacin in the growth medium. Growth of lomefloxacin resistant strains of *Escherichia coli* was studied in presence of different antibiotics by poison agar method to determine the cross-resistance. The lomefloxacin (third generation) resistant strains as expected were also resistant to first generation and second generation antibiotics (Table 4).

TABLE 4

Sensitivity pattern of lomefloxacin resistant cells of *E. coli*

| Mutant (Lom$^R$) strains of *E. coli* | Growth in poison agar medium containing | | | | | |
|---|---|---|---|---|---|---|
| | Lomefloxacin 1.5 μg/ml | Nalidixic Acid 50 μg/ml | Oxolinic Acid 5 μg/ml | Aorfloxacin 20 μg/ml | Ciprofloxacin 2 μg/ml | Sparfloxacin 20 μg/ml |
| CAL 101 | + | + | + | + | + | + |
| CAL 102 | + | + | + | + | + | + |
| CAL 103 | + | + | + | + | + | + |
| CAL 104 | + | + | + | + | + | + |
| CAL 105 | + | + | + | + | + | + |
| CAL 106 | + | + | + | + | + | + |
| CAL 107 | + | + | + | + | + | + |
| CAL 108 | + | + | + | + | + | + |
| CA8000 (WT) | − | − | − | − | − | − |

+ = Growth,
− = No growth,
WT = Wild Type

EXAMPLE 5

Bioevaluation of Thymol for Activity Against Lom$^R$ Mutants of *E. coli*

The mutants resistant to lomefloxacin were tested against thymol for sesnsitivity through the disc diffusion assays. As obvious from the Table 5, thymol was effective in killing all the Lom$^R$ mutant cells of *Escherichia coli* indicating its direct use as the advanced generation drug against drug resistant bacteria.

TABLE 5

Disk diffusion assay for determining the activity of thymol against lomefloxacin resistant mutants of *Escherichia coli*.

| Mutant (Lom$^R$) strains of *E. coli* | Thymol (inhibition zones in mm) | |
|---|---|---|
| | 50 μg/disc | 100 μg/disc |
| CAL 101 | 2.0 | 4.0 |
| CAL 102 | 3.0 | 5.0 |
| CAL 103 | 2.0 | 3.0 |
| CAL 104 | 1.0 | 1.5 |
| CAL 105 | 2.0 | 4.0 |
| CAL 106 | 2.0 | 4.0 |
| CAL 107 | 2.0 | 4.0 |
| CAL 108 | 3.0 | 5.0 |
| CA8000 | 3.0 | 5.0 |

Tr = activity in traces (< 0.5 mm),
WT = Wild Type

EXAMPLE 6

Evaluation of thymol for activity against nalidixic acid resistant mutants of *Mycobacterium smegmatis*.

Upon finding the encouraging results of affectivity of Thymol as antibacterial agent against various levels and kinds of drug resistance(s) developed in *E. coli* we planned the experiments in the *Mycobacterium* also. We employed *M. smegmatis*, the fast growing model system used for screening anti-tuberculosis drugs. A series of drug resistant mutants were isolated in the wild type strain MC$^2$. Initially nalidixic acid resistant strains were tested for sensitivity against thymol. The nalidixic acid mutants were isolated by growing the wild type strain of *Mycobacterium smegmatis* in medium containing 50 μg/ml nalidixic acid. As evident from Table 6, thymol could effectively kill Nal$^R$ strains of *Mycobacterium smegmatis* establishing its usefulness as an effective antibacterial drug even against mycobacteria.

TABLE 6

Disk diffusion assay for determining the activity of thymol against nalidixic acid resistant mutants of *Mycobacterium smegmatis*

| Mutant (Nal$^R$) strains of *Mycobacterium smegmatis* | Nalidixic acid | Thymol (inhibition zones in mm) | | |
|---|---|---|---|---|
| | 50 μg/disc | 50 μg/disc | 100 μg/disc | 250 μg/disc |
| MSN 101 | — | Tr. | 3 | 5 |
| MSN 102 | — | Tr. | 2 | 5 |
| MSN 103 | — | 1 | 2 | 5 |
| MSN 104 | — | 1 | 2 | 5 |
| MSN 105 | — | — | — | 2 |
| MSN 106 | — | 1 | 3 | 5 |
| MSN 107 | — | 1 | 3 | 6 |
| MSN 108 | — | 1 | 3 | 5 |
| MSN 109 | — | 1 | 2 | 5 |
| MSN 110 | — | 1 | 2 | 5 |
| MSN 111 | — | 1 | 2 | 5 |
| MSN 112 | — | 1 | 3 | 5 |
| MSN 113 | — | Tr. | 2 | 3 |
| MSN 114 | — | Tr. | 1.5 | 3 |
| MSN 115 | — | Tr. | 2 | 3 |
| MC$^2$ (WT) | — | 1 | 2 | 4 |

Tr = activity in traces (< 0.5 mm),
WT = Wild Type

EXAMPLE 7

Bioevaluation of thymol for activity against Lom$^R$ mutants of *Mycobacterium smegmatis*.

The lomefloxacin mutants were isolated by growing the wild type strain of *Mycobacterium smegmetis* in medium containing 20 μg/ml lomefloxacin (third generation antibiotic of the fluoroquinolone category). These mutants were resistant to lomefloxacin upto 60 μg/ml. It is important to note here that the level of resistance that emerges in the mycobacterial cells upon mutations is tremendously high compared to *E. coli* and the drugs that can kill such Lom$^R$ mutants will be of immense need and value. Interestingly these mutant were also found to be resistant against the second generation antibiotics like ciprofloxacin. These were then checked for the sensitivity against thymol, the compound of this invention, and as indicated in the Table 7 thymol effectively killed these multiple resistant cells of *Mycobacterium smegmatis* and thus supporting the inference that thymol can act as the fourth/advanced generation herbal antibiotic.

TABLE 7

Disk diffusion assay for determining the activity of thymol against lomefloxacin resistant mutants of *Mycobacterium smegmatis*.

| Mutant (Lom$^R$) strains of *Mycobacterium smegmetis*. | Lomefloxacin | Thymol (inhibition zones in mm) | |
|---|---|---|---|
| | 200 μg/disc | 100 μg/disc | 150 mg/ml |
| MSL 101 | — | 1 | 3 |
| MSL 102 | — | 1 | 3 |
| MSL 103 | — | 1 | 3 |
| MSL 104 | — | 1 | 3 |
| MSL 105 | — | 1 | 3 |
| MSL 106 | — | Tr. | 3 |
| MSL 107 | — | 1 | 3 |
| MSL 108 | — | 1 | 3 |
| MSL 109 | — | 1 | 2.5 |
| MSL 110 | — | 1 | 3 |
| MSL 111 | — | 1 | 3 |
| MSL 112 | — | 1 | 3 |
| MC$^2$ (WT) | — | 1 | 3 |

Tr = activity in traces (< 0.5 mm),
— = No activity,
WT = Wild Type

EXAMPLE 8

Activity of Thymol Against Bacterial Mutants Resistant to Another Frontline Anti-Tubercular Drug Isoniazid.

TABLE 8

Sensitivity of isoniazid resistant mutant cells of *escherichia coli* against thymol

| Strains of E. coli | Thymol (inhibition zones in mm) 100 μg/disc |
|---|---|
| CA8000 | 6 |
| CAO3 | 2 |
| CAO3 (revert) | 8 |

Isoniazid is another drug widely used for controlling tuberculosis as the bacteria is sensitive to this drug due to absence of oxyR system. Wild type *E. coli* strain is resistant to high concentration of antibiotic (1000 μg/ml). This strain was mutagenised by N'N-methyl Nitrosoguanidine to isolate the sensitive strain which is being killed at a concentration of 250 μg/ml in broth (CAO3). Further, a spontaneous mutation was detected from the sensitive mutant culture, which was resistant to 1000 μg/ml isoniazid. These cultures were tested for thymol sensitivity at a concentration of 100 μg/disc through disc diffusion assay and observed that the isoniazid resistant revertant strain (CAO3revert) was more sensitive.

EXAMPLE 9
Activity of Thymol Against Ethidium Bromide Resistant (mdr) Mutants

TABLE 9

| Strains of *Mycobacterium smegmetis*. | Thymol (100 μg/disc) |
|---|---|
| Wild type | 8 mm |
| Ethidium bromide resistant strain | 11 mm |

A mutant of *Mycobacterium smegmetis* was isolated by successive enrichment of the normally sensitive wild type strains upto 12 μg ethidium bromide/ml in broth. This mutant grow well at this concentration of ethidium bromide, while the wild type is killed at 3 μg ethidium bromide/ml in broth. Further, this ethidium bromide resistant strain was found to be multiply drug resistant (mdr) against antibiotics like Chloromphenicol (20 μg/ml), Tetracycline (10 μg/ml) and Rifampicin (40 μg/ml).

EXAMPLE 10
Activity of the Compound of the Present Invention Thymol at Different pH in *Escherchia coli* Strain CA8000.

TABLE 10

| Concentrations | pH (inhibition zone in mm) | | | |
|---|---|---|---|---|
| | 4.00 | 7.00 | 9.00 | 1M NaOH |
| 12.5 μg/disc | — | — | — | — |
| 25 μg/disc | trace | 1.00 | — | — |
| 50 μg/disc | 2.00 | 2.00 | 1.00 | 1.00 |
| 100 μg/disc | 4.00 | 6.00 | 3.00 | 2.00 |

The above table clearly indicate that the activity of the present compound is maximum at neutral pH (7.00).

EXAMPLE 11
Preparation of Synergistic Antibacterial Composition of Thymol Against Multidrug Resistant Bacteria.

From our study we observed that thymol is a potent bactericide agent against multidrug resistant bacteria. Further it was observed that the potency is increased by combining the oils from mlnts *Mentha arvensis* and *Mentha spicata*. The oil combination had Limonene (6.8–23.2%), Menthol(0.66–2.45%), Carvone(64.0–76.1%) and unidentified fractions in the essential oils totalling to 100% at different stages of growth. When this oil combination is used at a concentration of 0.1% of thymol the antibacterial activity of thymol is increased by 45%. Beside this the oil adds the pleasant carvone flavor to the composition with a menthol tinge. Considering this we prepared different compositions as follows.

TABLE 11

Disk diffusion assay for determining the synergistic effect of thymol with nalidixic acid against *E. coli* cells

| Nalidixic acid concentration (μg/disc) | Inhibition zone (in mm) of disc containing | | | Thymol concentration (μg/disc) |
|---|---|---|---|---|
| | Nalidixic acid | Combination (Nal + Thymol) | Thymol | |
| 0.25 | 3 | 4 | Tr | 12.5 |
| 0.50 | 6 | 12 | 2 | 25.0 |
| 1.00 | 9 | 10 | 3 | 50.0 |
| 1.50 | 11 | 10 | 5 | 75.0 |
| 2.00 | 12 | 10 | 6 | 100.0 |

Tr = activity in traces (< 0.5 mm),
WT = Wild Type

TABLE 12

Disk diffusion assay for determining the synergistic effect of thymol with Mentha hybrid oil against *E. coli* cells

| Mentha hybrid oil (μg/disc) | Inhibition zone (in mm) of disc containing | | | Thymol concentration (μg/disc) |
|---|---|---|---|---|
| | Mentha hybrid oil | Combination (Oil + Thymol) | Thymol | |
| 50 | 0 | 1.0 | 3.0 | 50 |
| 5 | 0 | 5.0 | 3.0 | 50 |
| 0.5 | 0 | 2.5 | 3.0 | 50 |

Composition 1
1. Thymol 100–500 mg (20–50% w/w)
2. Essential oil from the hybrid 0.1–0.5 mg
3. Citric acid 2–10 mg
4. Calcium carbonate 100–200 mg
5. Magnesium hydroxide gel 50–100 mg
6. Lactose 200–600 mg
7. Total weight 500–1000 mg The ingredients are mixed properly, powdered and packed in gelatin capsule available commercially in the market.

Composition 2
The essential oil is diluted 0 to 10 times.
1. Thymol 50–300 mg (10–60%) in essential oil combination.

These preparation are soaked in 250 mg lactose ball.

Composition 3
Honey is diluted 0 to 10 times in sterile distilled water and following ingredients added:
1. Thymol 50–300 mg (10–60%)
2. Essential oil combination from mints (0.1 to 1.0%)

Composition 4
1. Thymol 100–500 mg
2. Citric acid 2–10 mg

This two components are dissolved in 5 ml 0.05 M Sodium buffer (pH 7.0) containing 200 mg sodium glutamate.

What is claimed is:

1. A method for treating drug resistant bacterial infections comprising the steps of:

administering to a subject in need thereof a therapeutically effective amount of a formulation comprising an effective amount of thymol obtained from the plant *Trachyspermum ammi*, a mint oil containing an effective amount of monoterpenes obtained from a hybrid of *Mentha spicata* and *Mentha arvensis*, and additives, wherein the concentration of mint oil is in a range of about 0.1% to 0.5% w/w, and wherein the concentration of thymol is in a range of about 20 to 50% w/w.

2. A method as claimed in claim 1, wherein the formulation is administered orally or subcutaneously.

3. A method as claimed in claim 1, wherein the formulation is dissolved in 5 ml 0.05 M sodium buffer (pH 7.0) comprising 200 mg sodium glutamate and is applied as a subcutaneous injection.

4. A method as claimed in claim 1, wherein the formulation is effective against bacterial infections selected from the group consisting of enteric infections, and systemic infections.

5. A method as claimed in claim 1, wherein the method for treating drug resistant bacterial infections comprises administration of the formulation for bacterial infections caused by bacteria resistant to a drug selected from the group consisting of ethidium bromide, isoniazid, chloremphenicol, tetracycline, rifampicin, nalidixic acid, oxolinic acid, sparfloxicin, ciprofloxicin, and loamfloxicin.

6. A method as claimed in claim 1, wherein the drug resistant bacterial infections are caused by bacteria selected from the genus group consisting of *Mycobacterium*, and *Escherchia*.

* * * * *